United States Patent [19]

Jones

[11] 4,085,282

[45] Apr. 18, 1978

[54] PROCESS FOR PREPARING SUBSTITUTED TRIAZINES

[75] Inventor: John Arthur Jones, Belpre, Ohio

[73] Assignee: Borg-Warner Corporation, Chicago, Ill.

[21] Appl. No.: 744,669

[22] Filed: Nov. 24, 1976

[51] Int. Cl.$^2$ .......................................... C07D 251/70
[52] U.S. Cl. ................................................... 544/197
[58] Field of Search ...................................... 260/249.6

[56] References Cited

U.S. PATENT DOCUMENTS

| | | | |
|---|---|---|---|
| 2,167,804 | 8/1939 | Gubler et al. | 260/249.6 X |
| 2,273,117 | 2/1942 | Kranzlein et al. | 260/249.6 X |
| 2,720,480 | 10/1955 | Wolf | 260/249.6 X |
| 2,820,032 | 1/1958 | Hill et al. | 260/249.5 |
| 3,074,946 | 1/1963 | Rattenburg et al. | 260/249.5 |
| 3,164,592 | 1/1965 | Moergeli | 260/249.6 X |

OTHER PUBLICATIONS

Smolin et al., "The Chemistry of Heterocyclic Compounds" s–Triazines and Derivatives, Interscience Publishers (New York) 1959, pp. 55–57.

Chemical Abstracts 58, 4568e, (1963).

Azo & Anthaquinonoid Dyes Containing the Cyanuric Ring, Fierz–David; J. Soc. Dyes & Colorists, pp. 424–436 (1937).

*Primary Examiner*—John M. Ford
*Attorney, Agent, or Firm*—Joseph Shekleton

[57] ABSTRACT

A process for preparing substituted triazines. The process involves the reaction of cyanuric chloride with a polyhaloaniline under superatmospheric pressure.

11 Claims, No Drawings

PROCESS FOR PREPARING SUBSTITUTED TRIAZINES

The invention of this application relates as indicated to a process for preparing substituted triazines. More particularly, it relates to such a process which is characterized by the fact that it is carried out at superatmospheric pressure.

The substituted triazines which are formed by the process herein are tris-(polyhalophenylamino)triazines having the structure, e.g.,

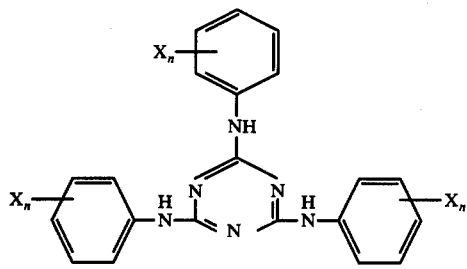

where X is halogen and $n$ is 1–5. The preparation of such compounds heretofore has been accomplished only with considerable difficulty and in relatively low yields. In copending application Ser. No. 707,155, filed July 21, 1976, now abandoned and assigned to the assignee of this application, it is taught that such compounds may be prepared by, first, heating a mixture of a polyhaloaniline and cyanuric chloride in a solvent at a temperature below 145° C, then reacting the intermediate product of such first step with additional polyhaloaniline at a higher temperature. The overall yield of 2,4,6-tris(2',4',6'-tribromophenylamino)-1,3,5-triazine obtained from such a procedure (see Example I of that application) is 27.8% of the theory. The process requires two steps and the total reaction time is about 30 hours.

The reaction of p-chloroaniline with cyanuric chloride at 290°–310° C "for long periods of time . . . induced side reactions and good results could not be obtained." Honda, Chemical Abstracts 58, 4568e (1963). The 2,4,6-tris(p-chloroanilino)-1,3,5-triazine was the desired product.

The process of the invention herein involves the preparation of tris-(polyhalophenylamino)triazines by reacting a polyhaloaniline with a cyanuric halide under superatmospheric pressure. The reaction proceeds according to the following illustrative equation:

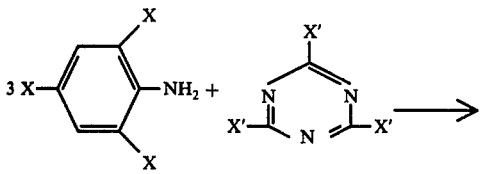

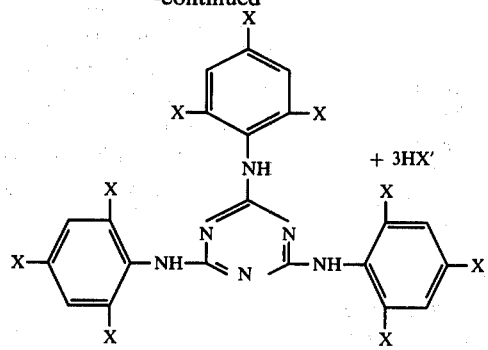

where X and X' are chlorine or bromine.

Although the process is applicable broadly as above it is most useful where X is bromine because of the special difficulty in preparing the tris-(polybromophenylamino)triazines by prior art methods; the process also is more applicable where X' is chlorine because of the greater availability of cyanuric chloride.

The process requires superatmospheric pressure. That is, it must be carried out in a closed system. Inasmuch as the reaction involves the formation of hydrogen chloride gas, the evolution of such gas will provide sufficient pressure very shortly after the reaction has begun. Thereafter, it is necessary only to vent excess hydrogen chloride so as to maintain the pressure at the desired level. In order to maintain the pressure uniformly throughout the process, nitrogen or some other inert gas may be admitted to the reaction vessel up to the desired pressure at the beginning of the reaction.

Virtually any superatmospheric pressure is beneficial to the process. Ordinarily, when the reaction is carried out on a laboratory scale in glass equipment, the pressure is maintained at about 10–40 psig. Higher pressures exceed the safety limits of glass reactors. On a larger scale, however, where metal reactors or glass-lined metal reactors are indicated, higher pressures are of course possible, up to 500 psig and higher.

The polyhaloaniline reactant may contain 1–5 halogen atoms. Illustrative species include 2-chloroaniline, 3-bromoaniline, 4-bromoaniline, 2,4-dichloroaniline, 2,6-dichloroaniline, 2,4,6-trichloroaniline, 2,3,4-trichloroaniline, 2,4,5,6-tetrachloroaniline, pentachloroaniline, 2,5-dibromoaniline, 3,5-dibromoaniline, 2,4,6-tribromoaniline, etc.

The temperature of the reaction may range from about 80° C to about 200° C. Preferably, the temperature is within the range of from about 125° C to about 175° C. The reaction conditions are maintained until the evolution of hydrogen chloride is substantially completed; generally the reaction is complete in 3–4 hours.

At least three mols of the polyhaloaniline per mol of cyanuric halide should be used and it is advisable to use more than this stoichiometric quantity so as to assure a maximum yield of completely substituted triazine product. Any excess polyhaloaniline can be recovered and used again.

A valuable feature of the process is the fact that it may be carried out in the absence of a solvent.

The process of the invention is illustrated by Examples I and II which follow. They are of course merely illustrative and should not be construed as limiting in any way whatsoever. Examples III and IV are set forth for the purpose of permitting a comparison with processes carried out at atmospheric pressure. It will be noted that the first two procedures (Examples I and II which exemplify the process of the invention) result in yields of 82.0% and 104.3% of the theory whereas the baseline procedures (Examples III and IV) result in yields of 45.0% and 59.7% of the theory.

These yields are calculated from liquid chromatograms by estimating the area under the curves which characterize the desired product.

EXAMPLE I

A mixture of 29.5 g. (0.16 g mol) of cyanuric chloride and 316.6 g. (0.96 g mol) of 2,4,6-tribromoaniline is charged to a pressure reactor which then is purged with nitrogen. Then, at a nitrogen pressure of 30 psig, the temperature is maintained at 138°–147° C for 4 hours (with continual stirring); the pressure is maintained at 30 psig throughout this period. The product mixture is dissolved in tetrahydrofuran, diluted with an equal volume of heptane, and concentrated to a small volume which then is cooled and filtered. The solid weighs 143.7 g. and is identified as containing about 92.7% (or 133.2 g.) the desired 2,4,6-tris-(2',4',6'-tribromophenylamino)-1,3,5-triazine, by liquid chromatographic analyses and elemental analyses.

The filtrate is concentrated to dryness yielding 181.0 g. of solid; it is shown, by the same means, to contain about 3.5% (or 6.3 g.) of the above desired product. The total yield of 2,4,6-tris-(2',4',6'-tribromophenylamino)-1,3,5-triazine is 139.5 g. or 82.0% of the theory.

EXAMPLE II

The procedure of Example I is repeated except that the temperature of the reaction mixture is maintained at 145°–155° C. The yield of 2,4,6-tris-(2',4',6'-tribromophenylamino)-1,3,5-triazine is 177.6 g. or 104.3% of the theory.

EXAMPLE III

The procedure of Example I was repeated except that the reaction pressure is maintained at 0 psig and the temperature of the reaction mixture is maintained at 147°–156° C. The yield of 2,4,6-tris-(2',4',6'-tribromophenylamino)-1,3,5-triazine is 76.7 g. or 45.0% of the theory.

EXAMPLE IV

The procedure of Example I is repeated except that the reaction pressure is maintained at 0 psig and the temperature of the reaction mixture is maintained at 146°–153° C. The yield of 2,4,6-tris-(2',4',6'-tribromophenylamino)-1,3,5-triazine is 99.8 g. or 59.7% of the theory.

All parts and percentages herein are by weight unless specifically stated to be otherwise.

I claim:

1. A process for preparing tris-(polyhalophenylamino)triazines comprising reacting a polyhaloaniline with a cyanuric halide under superatmospheric pressure.

2. The process of claim 1 wherein the polyhaloaniline is a polybromoaniline.

3. The process of claim 1 wherein the polyhaloaniline is 2,4,6-tribromoaniline.

4. The process of claim 1 wherein the cyanuric halide is cyanuric chloride.

5. A process for preparing tris-(polyhalophenylamino)-triazines comprising preparing a mixture of a stoichiometrically excessive amount of a polyhaloaniline and a cyanuric halide and heating said mixture under superatmospheric pressure.

6. The process of claim 5 wherein the superatmospheric pressure is initially a superatmospheric pressure of nitrogen.

7. The process of claim 5 wherein the polyhaloaniline is a polybromoaniline.

8. The process of claim 5 wherein the cyanuric halide is cyanuric chloride.

9. The process of claim 5 wherein said mixture is heated at a temperature of from about 125° C to about 200° C.

10. The process of claim 5 wherein the superatmospheric pressure is within the range of from about 10 to about 40 psig.

11. The process of claim 5 wherein the polyhaloaniline is 2,4,6-tribromoaniline.

* * * * *